United States Patent [19]
Linden et al.

[11] Patent Number: 5,323,772
[45] Date of Patent: Jun. 28, 1994

[54] RESPIRATOR HAVING AN INSPIRATION GAS FLOW CONTROLLED BY THE EXPIRATION GAS FLOW

[75] Inventors: Dan Linden, Stockholm; Sven-Gunnar Olsson, Arloev, both of Sweden

[73] Assignee: Siemens Aktiengesellschaft, Munich, Fed. Rep. of Germany

[21] Appl. No.: 890,854

[22] Filed: Jun. 1, 1992

[30] Foreign Application Priority Data

Jun. 28, 1991 [EP] European Pat. Off. ......... 91110801.7

[51] Int. Cl.⁵ ............................................. A61M 16/00
[52] U.S. Cl. ........................... 128/204.23; 128/204.21; 128/205.13
[58] Field of Search ................. 128/204.21, 204.22, 128/205.11, 205.13, 205.17, 204.28, 204.23

[56] References Cited

U.S. PATENT DOCUMENTS

| | | | |
|---|---|---|---|
| 3,741,208 | 6/1973 | Jonsson . | |
| 3,840,006 | 10/1974 | Buck . | |
| 4,323,064 | 4/1982 | Hoenig | 128/204.21 |
| 4,340,044 | 7/1982 | Levy | 128/204.21 |
| 4,345,612 | 8/1982 | Koni | 137/101.19 |
| 4,380,233 | 4/1983 | Caillot | 128/204.21 |
| 4,838,257 | 6/1989 | Hatch | 128/204.18 |

FOREIGN PATENT DOCUMENTS

| | | | |
|---|---|---|---|
| 0117699 | 9/1984 | European Pat. Off. | 128/204.21 |
| 0256171 | 2/1988 | European Pat. Off. | 128/204.21 |
| 0402951 | 12/1990 | European Pat. Off. | |
| 0459647 | 12/1991 | European Pat. Off. | |
| 2079984 | 1/1982 | United Kingdom | 128/204.21 |

OTHER PUBLICATIONS

"Microelectronic Circuits", Adel Sedra et al., Holt Rinehart & Winston, 1982 pp. 155–157; 522–523.
Siemens Servo Ventilator 900 C Training Instructions.
Siemens Servo Ventilator 900 C Key to Training Instructions.

*Primary Examiner*—Edgar S. Burr
*Assistant Examiner*—Eric P. Raciti
*Attorney, Agent, or Firm*—Hill, Steadman & Simpson

[57] ABSTRACT

In a respirator having an inspiration gas flow controlled by the expiration gas flow, in order to avoid triggering difficulties, particularly in the neonatal respiration therapy, the respirator is controlled such that a continuous gas flow flows through the inspiration and expiration lines. The gas flow is measured in the inspiration line by a gas flow sensor. The measured signal from the gas flow sensor is used to control a valve in the inspiration line, or a common line connected to the inspiration and expiration lines so that a constant gas flow is maintained in the expiration line.

12 Claims, 3 Drawing Sheets

RESPIRATOR HAVING AN INSPIRATION GAS FLOW CONTROLLED BY THE EXPIRATION GAS FLOW

BACKGROUND OF THE INVENTION

1. Field of the Invention

The present invention is directed to a respirator of the type having an inspiration gas flow which is controlled by the expiration gas flow.

2. Description of the Prior Art

A respirator of the type described above is described in the Training Manual for the Servo Ventilator 900 C, manufactured by Siemens. Various respiration modes can be set using this ventilator. One of these modes is spontaneous respiration with continuous positive aspiration airway pressure (CPAP). CPAP is particularly used in neonatal respiratory care. Initiation of the inspiration phase in this mode is triggered by the patient when, for example given an inhalation attempt by the patient, the pressure in the expiration line falls below an adjustable level. The inspiration valve then opens and breathing ensues without further assistance by the ventilator, i.e., the patient controls, among other things, the breathing rate and the tidal volume. The inspiration is ended, and expiration is initiated, in a similar manner dependent on certain parameters. During the entire time, the expiration valve regulates the expiration pressure to a set PEEP (positive end-expiratory pressure) value, so that a continuous, positive respiratory path pressure is maintained.

Instead of pressure-dependent triggering, it is also known to trigger the ventilator given defined changes in the gas flow.

When providing respiratory therapy to infants and, in particular, premature babies, such triggering may be difficult under certain circumstances. Given pressure-controlled triggering, the infant must first produce a certain under-pressure before the ventilator starts a new inspiration phase. This necessary exertion can complicate the treatment of such infants. Additionally, disturbing delays can arise when switching a respirator of the type described above from the expiration phase to inspiration phase, because the gas column which is present in the gas lines between patient and the ventilator has a certain inertia, which must be overcome. An undesired time thus passes until fresh respiratory gas proceeds from the inspiration line to the airways and lungs of the patient when switching from the expiration phase to the inspiration phase.

SUMMARY OF THE INVENTION

It is an object of the present invention to provide a respirator of the type described above with improved operation so that the aforementioned difficulties associated with triggering are avoided.

The above object is achieved in accordance with the principles of the present invention in a ventilator (respirator) wherein the respirator is controlled so that a continuous gas flow exists through the inspiration and expiration lines. The gas flow is measured in the expiration line by a gas flow sensor. The value from the sensor is used to control the inspiration valve so that a substantially constant gas flow is maintained through the expiration line. As a result, switching between inspiration and expiration dependent on trigger levels is substantially no longer undertaken. When the patient inhales, the flow through the expiration line would normally drop. This is immediately registered by the gas flow sensor in this line, in accordance with the principles of the invention. Dependent on this signal, the valve in the inspiration line is opened such that the flow through the inspiration line is increased, and the gas flow through the expiration line is maintained at a substantially constant level. When the patient exhales, the apparatus reacts conversely.

In an embodiment of the invention, the adjustable level for the gas flow in the expiration line corresponds to a bypass gas flow, which is maintained during the time the patient is neither inhaling nor exhaling. When the gas flow in the expiration line upwardly exceeds the adjusted level, the extent to which the inspiration valve is opened is reduced according to a prescribable time function, independently of the difference between the actual gas flow in the expiration line and the adjusted level. During expiration, for example, it is thus possible to decrease the gas flow in the inspiration line according to a known function, or to even keep it constant. The overall expiratory volume can thus be identified in a more simple way by measuring the gas flows both in the inspiration and in the expiration lines, because substantially no fluctuations of the gas flow in the inspiration line occur.

A simple control of the inspiration gas flow dependent on the expiration gas flow is achieved in accordance with the principles of the present invention in a respirator having a regulator with negative feedback. A signal corresponding to the adjusted level is supplied to the regulator as the actual value, and the signal of the flow sensor is supplied to the regulator as the rated or desired value. The output signal from this regulator can be directly employed for controlling the inspiration valve. Preferably, however, the control of the inspiration valve ensues through a further regulator, to which the output signal of the first regulator is supplied as the reference signal or rated value. The regulator may be an integrator regulator (I-regulator). The use of such a regulator means that a brief-duration flow fluctuation at the expiration site will have substantially no influence on the control, so that overshooting of the regulator is substantially avoided.

DESCRIPTION OF THE PREFERRED EMBODIMENTS

Figure 1:
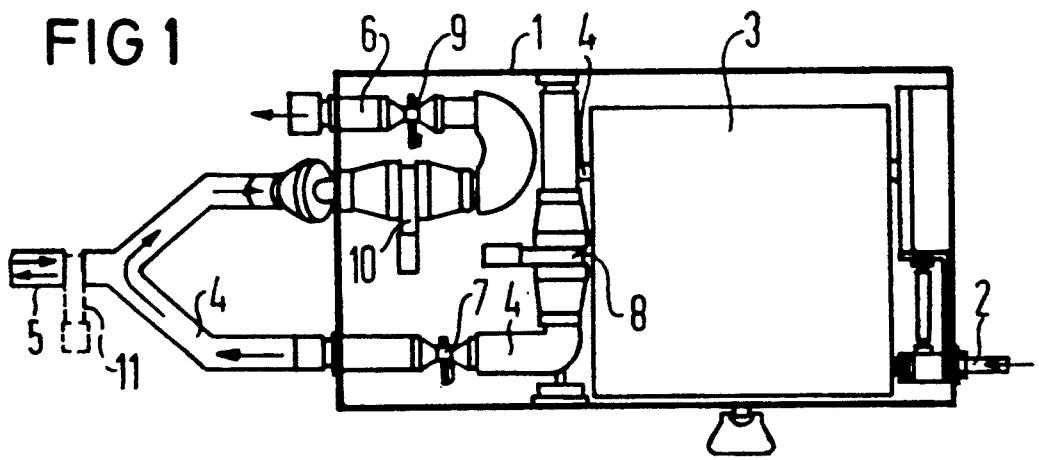
FIG. 1 is a plan view of a ventilator constructed in accordance with the principles of the present invention, with one side removed to exposed the mechanical components thereof.

The basic mechanical/pneumatic components of a respirator 1 constructed in accordance with the principles of the present invention are shown in FIG. 1. The respiratory gas proceeds via a line 2 into a reservoir 3, for example a bellows. From the reservoir 3, the respiratory gas is supplied via an inspiration line 4 to a further line 5 connected to a patient (not shown). The line 5 is also in communication with an expiration line 6. The arrows in the lines indicate the direction of gas flow therein. The inspiration line 4 is provided with a valve 7 and a gas flow sensor 8. The expiration line 6 is also provided with a valve 9 and a gas flow sensor 10. Additionally, a pressure sensor (not shown) may also be connected in each line. The signals from the flow or, (effused) pressure sensors are conducted to a control unit (not shown) which controls the opening and closing of the valves 7 and 9 dependent on the sensor signals, and dependent on the mode of respiration which has been selected and on the given boundary conditions. A gas flow sensor 11, shown with dashed lines, can also being connected in the line 5, which generates a signal that is also supplied to the control unit.

Figure 2:
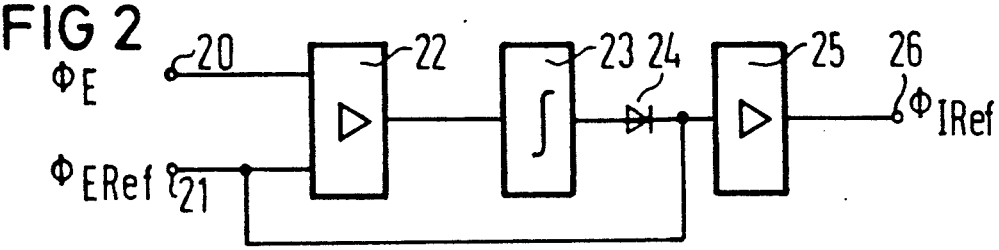
FIG. 2 is a block circuit diagram for a control circuit for the inspiration gas flow, for use in the ventilator of FIG. 1, constructed in accordance with the principles of the present invention.

The basic principle of the respirator in accordance with the principles of the present invention is shown in block diagram form in FIG. 2. A signal corresponding to the gas flow $\Phi_E$ in the expiration line is supplied at a terminal 20. A reference signal corresponding to the set level of the desired gas flow $\Phi_{ERef}$ in the expiration line is supplied to a terminal 21. The difference between these two signals, i.e., the deviation of the actual flow from the set flow, is formed in a differential amplifier 22, and may also be amplified under certain circumstances. This difference signal is connected to a subsequent integrator 23, whose output signal is supplied to a further amplifier 25 via a diode 24. The reference signal is also supplied to the further amplifier 25. A signal $\Phi_{IRef}$ which is employed for controlling the valve in the inspiration line is present at the output of this amplifier 25.

The functioning of this circuit is as follows. If it is first assumed that the actual flow $\Phi_E$ is at the set level, the difference will be zero and thus the output signal of the amplifier 22 is zero. The integrator 23 thus does not generate an output signal. The only input signal at the amplifier 25 is thus the reference signal which, after amplification, serves the purpose of controlling the valve 7 in the inspiration line, and maintains the flow through this valve constant. When it occurs, for example due to an attempt by the patient to inhale, that $\Phi_E$ drops in comparison to $\Phi_{ERef}$, the difference is amplified and integrated and, as long as the integration value is positive, the difference is forwarded via the diode 24 to the amplifier 25, and is added to the reference signal. The output signal $\Phi_{IRef}$ is thus modified relative to the fixed level dependent on the actual gas flow through the expiration line. The modification results in the gas flow at the inspiration line being increased, in order to compensate for the removal of gas by the patient and to again boost the gas flow at the expiration side to the established level.

It is possible within the scope of the invention to omit the diode 24 shown in FIG. 2, and thus to have the gas flow at the inspiration side follow the gas flow at the expiration side in both directions. This would then result, given a decreasing gas flow in the expiration line, in an increase in the gas flow in the inspiration line, and vice versa. Due to the presence of the diode 24, however, adjustment of the inspiration flow is substantially limited to the inspiration phase, i.e., to the phase wherein the gas flow in the expiration line attempts to drop below the established level due to efforts by the patient to inhale. During the expiration phase, a defined value for the inspiration gas flow is provided which is not subject to sudden fluctuations, thereby facilitating a calculation of the overall expiratory volume.

Figure 3:
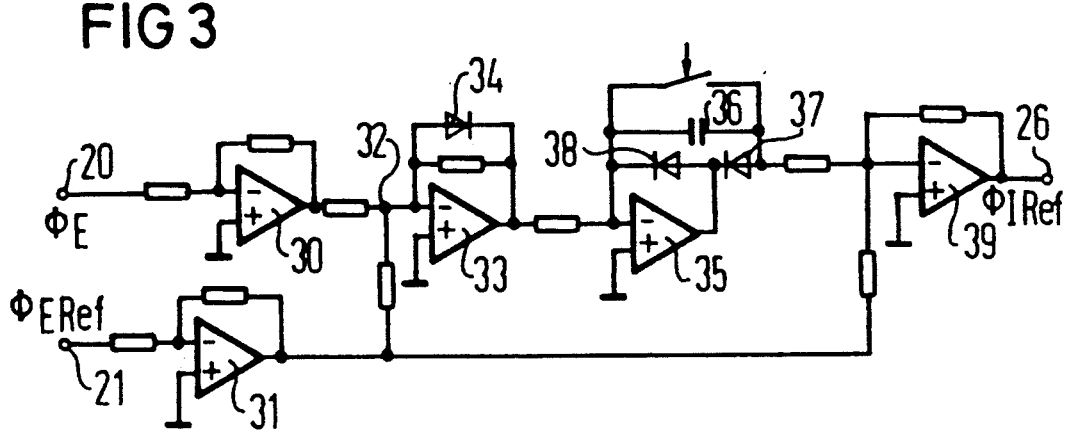
FIG. 3 is a circuit diagram for one embodiment of the block circuit of FIG. 2.

An exemplary circuit for generating a control value for the valve 7 in the inspiration line, based on the block diagram shown in FIG. 2, is shown in FIG. 3. The signal corresponding to the actual flow $\Phi_E$ is supplied to a first amplifier 30 via the terminal 20. The reference signal $\Phi_{ERef}$ is supplied via a terminal 21 to an amplifier 31. Both amplifiers 30 and 31 are for signal editing. The outputs of these two amplifiers are combined at point 32, so that a signal is present at the point 32 corresponding to the difference of the output signals of the two amplifiers 21 and 31. Polarity and gain factors are selected so that the difference becomes zero when the actual flow corresponds to the set flow. The signal at point 32 is supplied to an amplifier 33, essentially corresponding to the amplifier 22 of FIG. 2. A diode 34 is connected in parallel with a resistor in a feedback branch of this amplifier. The diode 34 becomes blocking given a negative input voltage at the amplifier 33, and the amplification ensues according to the resistances which have been selected. An amplified signal is present at the output of the amplifier 33 which is inverted with respect to the input for that amplifier. If, by contrast, the input signal becomes positive, the diode 34 becomes transmissive and a constant output level of, for example, $-0.6$ volts is present at the output of the amplifier 33, independently of the size of the input signal.

The output signal of the amplifier 33 is supplied to an integrator 35 which corresponds to the integrator 23 of FIG. 2. A capacitor 36 is connected in series with a diode 37 in the feedback branch of the integrator 35. A further diode 38 is connected in parallel with the diode 37 and the capacitor 36. As long as the input signal at the integrator 35 is positive, the diode 38 is in a blocking state, and the capacitor 36 is charged. If the negative voltage, (i.e., $-0.6$ volts) is present at the input, the capacitor 36 is discharged with this constant voltage, but is not charged in an opposite direction because the diode 38 is then transmissive.

The output of the integrator 35 is supplied to a further amplifier 39, to which the reference signal $\Phi_{ERef}$ from the amplifier 31 is simultaneously supplied. The sum of this amplified reference signal and the output signal of the integrator 35 is thus present at the input of the amplifier 39. This sum, after amplification by the amplifier 39, represents the reference signal $\Phi_{IRef}$ at the terminal 26 for controlling the extent to which the valve 7 in the inspiration line is opened.

As mentioned above, the diodes 34, 37 and 38 can be omitted and the change in the gas flow in the expiration line in both directions can be correspondingly compensated, both positively and negatively, by changing the inspiration gas flow. Moreover, it is possible within the scope of the invention to add further controls, such as a proportional control, in addition to the integral control, or to replace the integral control by a proportional control.

Further regulation via a negative feedback loop can be provided for controlling the valve 7 by monitoring the difference between a signal from the gas flow sensor 8 in the inspiration line 4 and a reference signal, and through feedback causing this difference to tend toward zero. The output of the amplifier 39, i.e., the signal $\Phi_{IRef}$, can be used as this further reference signal, so that the difference between the flow as measured by the gas flow sensor 8 and $\Phi_{IRef}$ is maintained at or close to zero.

Figure 4A:
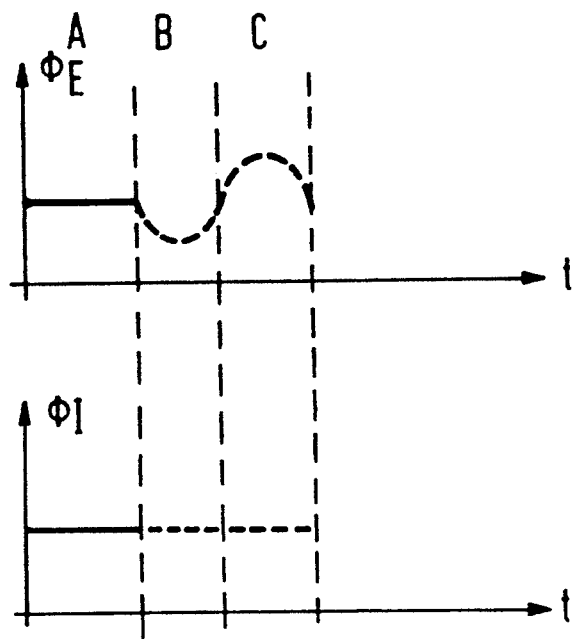
FIGS. 4A and 4B are schematic representations of the chronological curve of the gas flows through the expiration and inspiration lines in accordance with the principles of the present invention.
Figure 4B:
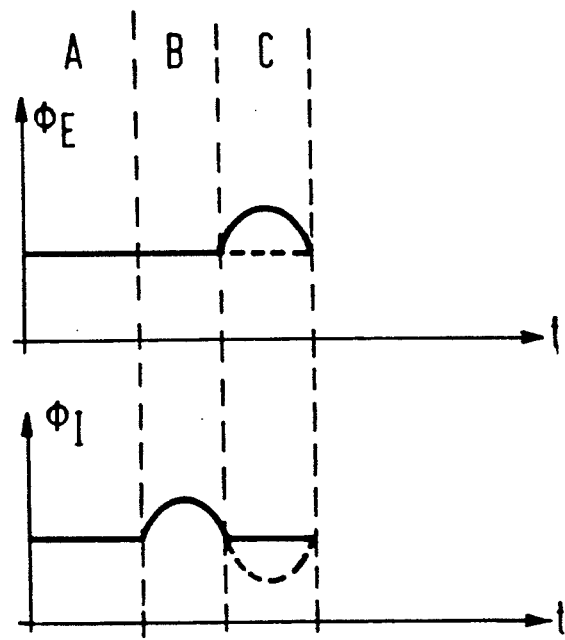

The respective gas flows in the expiration and inspiration lines are entered over time in each of FIGS. 4A and 4B. The time axis is subdivided into three sections A, B and C.

It is assumed in section A in FIG. 4A that the patient gas flow is zero, i.e., the patient is neither inhaling nor exhaling. In this case, the expiration gas flow $\Phi_E$ is equal to the inspiration gas flow $\Phi_I$, and is constant. The patient gas flow is negative in section B, i.e., the patient is inhaling. If it is assumed that the inspiration gas flow continues to remain constant, as indicated with dashed lines in the lower part of FIG. 4A, the expiration gas flow will then drop in accord with the negative patient gas flow. This is also indicated with dashed lines. It is assumed in section C that the patient gas flow is positive, i.e., the patient is exhaling. Again given the assumption that the inspiration gas flow is maintained constant, the expiration gas flow now increases accordingly.

The gas flows for the respirator of the invention are shown in FIG. 4B. The flows in section A are the same as shown in FIG. 4A. In section B, however, the expiration gas flow in FIG. 4B remains constant, because the inspiration gas flow is correspondingly increased for compensation, beginning with the first deviation from this constant level. In section C having a positive patient gas flow, the expiration gas flow in FIG. 4B increases in accord with the preferred exemplary embodiment, and the inspiration gas flow is maintained constant. It is also possible within this region, as shown with dashed lines, that the control takes affect and holds the expiration gas flow constant.

Figure 5:
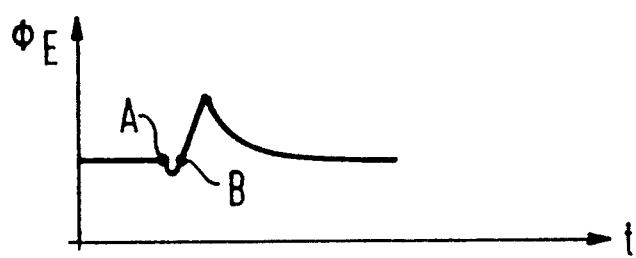
FIG. 5 shows the actual chronological curve of the gas flows through the expiration and inspiration lines, in accordance with the principles of the present invention.
Figure 5:
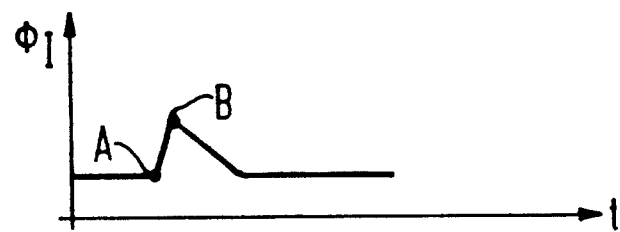

FIGS. 4A and 4B show the chronological curve of the gas flows schematically. FIG. 5 is an example of the curve of an actual expiration gas flow and an actual inspiration gas flow.

Again, a constant gas flow is established, i.e., the patient is neither inhaling nor exhaling. The patient begins to inhale at point A in FIG. 5. This initially results in a brief drop of the expiration gas flow and to an increasing inspiration gas flow, according to the control produced by the invention. At point B, the expiration gas flow again reaches the prescribed, constant level. Beginning at this time, the inspiration gas flow (which is not excessively high) drops according to a prescribed time function, which is a linear function in the example of FIG. 5, whereas the expiration gas flow initially continues to rise, but then also returns to the prescribed level.

The breathing volume of the patient can be calculated by integrating the difference between the two gas flows.

It is also possible within the scope of the present invention to control the valve 7 in the inspiration line on the basis of the patient gas flow, instead of by means of the gas flow through the expiration line. When the patient gas flow is negative, i.e., when the patient is inhaling, the inspiration valve is correspondingly opened. When the patient gas flow is positive, opening of the inspiration valve either remains constant, or changes according to a prescribable time function, or changes dependent on the patient gas flow. The patient gas flow can be identified with the gas flow sensor 11 in the common line 5 as shown in FIG. 1.

Although further modifications and changes may be suggested by those skilled in the art, it is the intention of the inventors to embody within the patent warranted hereon all changes and modifications as reasonably and properly come within the scope of their contribution to the art.

We claim as our invention:
1. A respirator comprising:
    an inspiration line and an expiration line each connectable to the airways of a patient;
    a source of respiratory gas;
    valve means in said inspiration line for setting a flow of respiratory gas from said source to said patient;
    at least one gas flow sensor disposed for sensing a gas flow in said expiration line; and
    control means, connected to said valve means and to said gas flow sensor, consisting of means for controlling said valve means dependent on a signal from said gas flow sensor for increasing gas flow through said inspiration line, and means, upon the occurrence of a decrease of gas flow in said expiration line below a selected level as sensed by said gas flow sensor, for bringing the gas flow in said expiration line back to said level.

2. A respirator as claimed in claim 1 wherein said control means comprises means for controlling said valve means to maintain a bypass gas flow when said patient is neither inhaling nor exhaling, and wherein said selected level corresponds to said bypass gas flow.

3. A respirator as claimed in claim 1 wherein said control means comprises means for, upon said gas flow in said expiration line upwardly exceeding said selected level, reducing the opening of said valve means independently of the difference between said gas flow in said expiration line and said selected level.

4. A respirator as claimed in claim 1 wherein said gas flow sensor is disposed in said expiration line.

5. A respirator as claimed in claim 1 further comprising a common line connected to both of said inspiration line and said expiration line and leading to said patient, and wherein said gas flow sensor is disposed in said common line.

6. A respirator as claimed in claim 1 wherein said control means includes a regulator with negative feedback supplied with a reference signal corresponding to said selected level and supplied with said signal from said gas flow sensor, and said regulator generating an output signal or controlling said valve means dependent on the difference between said reference signal and said signal from said gas flow sensor.

7. A respirator as claimed in claim 6 wherein said regulator is an integral regulator.

8. A respirator as claimed in claim 6 wherein said regulator includes means, dependent upon the polarity of said difference, for changing said output signal over time independently of the size of said difference.

9. A respirator as claimed in claim 6 wherein said regulator comprises:
    first amplifier means supplied with said reference signal and said signal from said gas flow sensor for forming said difference between said reference signal and said signal from said gas flow sensor;
    integrator means, supplied with said difference from said first amplifier means, for integrating said difference over time; and
    second amplifier means supplied with a combined signal formed by a the sum of said reference signal and the output of said integrator means for generating said output signal for controlling said valve means.

10. A respirator as claimed in claim 9 further comprising:
a further gas flow sensor disposed in said inspiration line; and negative feedback control loop means supplied with said output signal from said second amplifier means and with a signal from said further gas flow sensor for generating an additional control signal for said valve means such that a difference between said output signal from said second amplifier and said signal from said further gas flow sensor tends toward zero.

11. A respirator as claimed in claim 9 further comprising a diode connected between said integrator means and said second amplifier with a polarity for preventing the output of said integrator means from reaching said second amplifier means if the output of said integrator means is positive.

12. A respirator as claimed in claim 9 wherein said first amplifier means is an operational amplifier having a feedback branch with a resistor and diode connected in parallel.

* * * * *